(12) United States Patent
Castro et al.

(10) Patent No.: US 6,436,141 B2
(45) Date of Patent: Aug. 20, 2002

(54) APPARATUS FOR FUSING ADJACENT BONE STRUCTURES

(75) Inventors: Salvatore Castro, Milford, MA (US); Christopher McDonnell, Sandy Hook, CT (US)

(73) Assignee: Surgical Dynamics, Inc., Norwalk, CT (US)

( * ) Notice: Subject to any disclaimer, the term of this patent is extended or adjusted under 35 U.S.C. 154(b) by 0 days.

(21) Appl. No.: 09/788,693

(22) Filed: Feb. 20, 2001

Related U.S. Application Data

(63) Continuation-in-part of application No. 09/545,320, filed on Apr. 7, 2000.

(51) Int. Cl.⁷ .................................................. A61F 2/44
(52) U.S. Cl. .................................. 623/17.11; 623/16.11
(58) Field of Search ........................... 623/16.11–17.11

(56) References Cited

U.S. PATENT DOCUMENTS

| 4,743,256 A | 5/1988 | Brantigan |
| 4,772,287 A | 9/1988 | Ray et al. |
| 4,834,757 A | 5/1989 | Brantigan |

(List continued on next page.)

FOREIGN PATENT DOCUMENTS

| DE | 4302397 A1 | 2/1993 |
| DE | 350567 A1 | 2/1995 |
| EP | 07 32 093 A2 | 2/1995 |
| EP | 07 34 703 A2 | 3/1996 |

OTHER PUBLICATIONS

Methods of Lumbar Fusion, Norman W. Hoover, Jan. 1968.

Intervertebral Body Fusion by the Use of Posterior Bone Dowel, Wiltberger.

Primary Examiner—Corrine McDermott
Assistant Examiner—Thomas Barrett

(57) ABSTRACT

An apparatus for facilitating fusion of adjacent bony structures includes an implant body dimensioned for positioning between adjacent bone structures to maintain the bone structures in desired spaced relation during interbody fusion. The implant body has an outer wall and an external threaded configuration disposed on the outer wall. At least one concave surface at least partially extends along the implant body. The concave surface advantageously reduces the transverse cross-sectional dimension of the implant member thereby facilitating placement of the implant member in restricted intervertebral areas. In addition, the concave surface enables placement of a pair of implants in nested side-by-side relation. Preferably, the threaded configuration has portions removed along an arc section of the outer wall thereby defining a series of generally longitudinally aligned concave surfaces in individual turns thereof. A system and method for facilitating fusion of adjacent vertebrae is also disclosed.

9 Claims, 5 Drawing Sheets

U.S. PATENT DOCUMENTS

| | | | | |
|---|---|---|---|---|
| 4,878,915 A | | 11/1989 | Brantigan | |
| 4,961,740 A | | 10/1990 | Ray et al. | |
| 5,026,373 A | | 6/1991 | Ray et al. | |
| 5,055,104 A | * | 10/1991 | Ray | 606/61 |
| 5,192,327 A | | 3/1993 | Brantigan | |
| 5,423,817 A | | 6/1995 | Lin | |
| 5,425,722 A | | 6/1995 | Brantigan | |
| 5,458,638 A | | 10/1995 | Kuslich | |
| 5,489,307 A | | 2/1996 | Kuslich et al. | |
| 5,489,308 A | * | 2/1996 | Kuslich et al. | 623/17 |
| 5,505,732 A | | 4/1996 | Michelson | |
| 5,562,736 A | | 10/1996 | Ray et al. | |
| D377,095 S | | 12/1996 | Michelson | |
| 5,593,409 A | | 1/1997 | Michelson | |
| 5,609,636 A | | 3/1997 | Kohrs et al. | |
| 5,645,598 A | * | 7/1997 | Brosnahan | 623/17 |
| 5,653,763 A | | 8/1997 | Errico et al. | |
| 5,665,122 A | | 9/1997 | Kambin | |
| 5,669,909 A | | 9/1997 | Zdeblick et al. | |
| 5,683,463 A | | 11/1997 | Godefroy et al. | |
| 5,700,291 A | | 12/1997 | Kuslich et al. | |
| 5,709,683 A | | 1/1998 | Bagby | |
| 5,720,748 A | | 2/1998 | Kuslich et al. | |
| 5,772,661 A | | 6/1998 | Michelson | |
| 5,782,919 A | | 7/1998 | Zdeblick et al. | |
| 5,785,710 A | | 7/1998 | Michelson | |
| 5,797,909 A | | 8/1998 | Michelson | |
| 5,800,550 A | | 9/1998 | Sertich | |
| 6,010,502 A | | 1/2000 | Bagby | |
| 6,033,405 A | | 3/2000 | Winslow et al. | |
| 6,042,582 A | | 3/2000 | Ray | |
| 6,063,088 A | | 5/2000 | Winslow et al. | |
| 6,074,423 A | * | 6/2000 | Lawson | 623/17 |
| 6,080,155 A | | 6/2000 | Michelson | |
| 6,083,225 A | | 7/2000 | Winslow et al. | |
| 6,096,038 A | | 8/2000 | Michelson | |
| 6,113,602 A | | 9/2000 | Sand | |
| 6,120,503 A | | 9/2000 | Michelson | |
| 6,123,705 A | | 9/2000 | Michelson | |

* cited by examiner

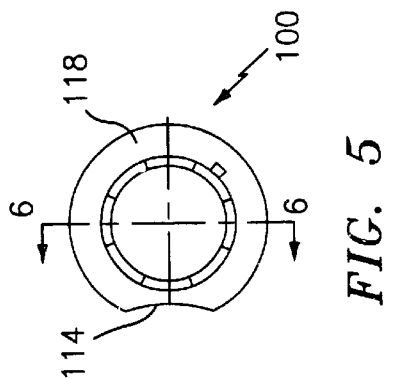
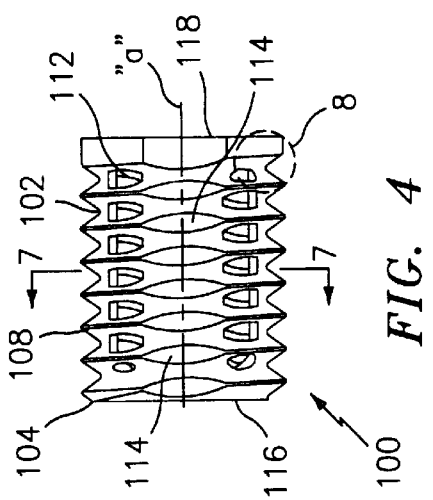
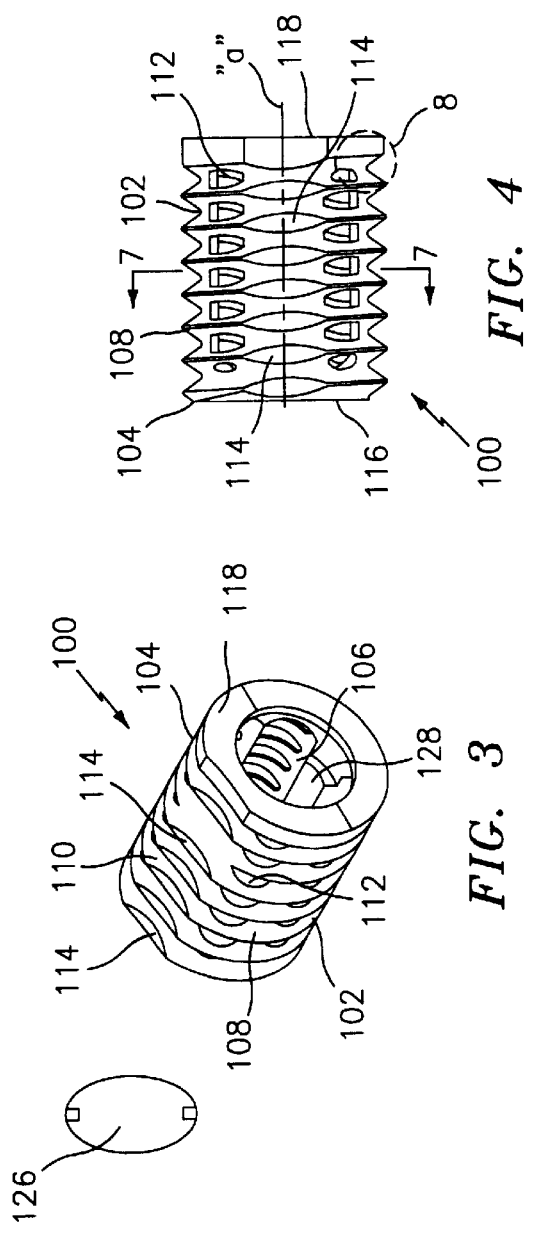
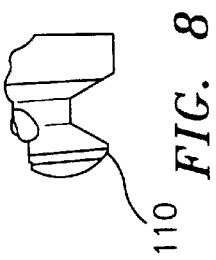
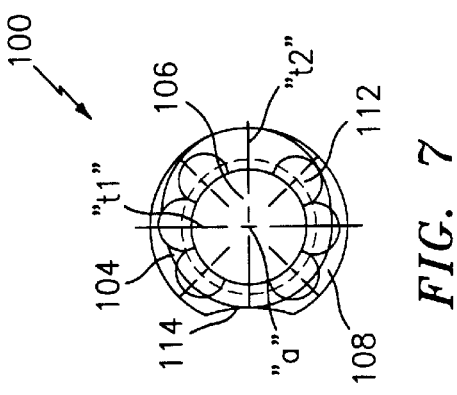
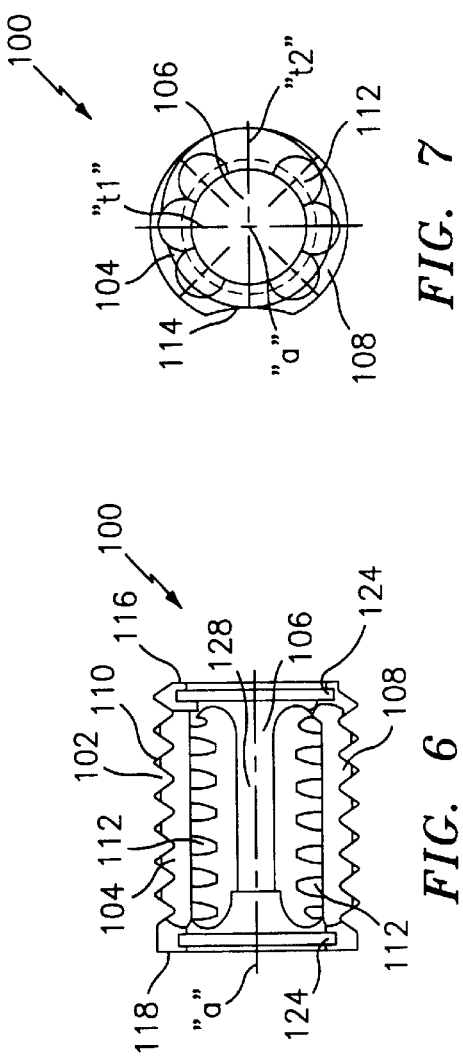

APPARATUS FOR FUSING ADJACENT BONE STRUCTURES

CROSS REFERENCE TO RELATED APPLICATIONS

This application is a Continuation-in-Part application of co-pending U.S. application Ser. No. 09/545,320 filed on Apr. 7, 2000.

BACKGROUND

1. Technical Field

The present disclosure generally relates to a surgical apparatus for fusing adjacent bone structures, and, more particularly, to an apparatus and associated method for fusing adjacent vertebrae.

2. Background of the Related Art

The fusion of adjacent bone structures is commonly performed to provide for long-term replacement to compensate for degenerative or deteriorated disorders in bone. For example, an intervertebral disc, which is a ligamentous cushion disposed between adjacent vertebrae, may undergo deterioration as a result of injury, disease, tumor or other disorders. The disk shrinks or flattens leading to mechanical instability and painful disc translocations.

Conventional procedure for disc surgery include partial or total excision of the injured disc portion, e.g., discectomy, and replacement of the excised disc with biologically acceptable plugs or bone wedges. The plugs are driven between adjacent vertebrae to maintain normal intervertebral spacing and to achieve, over a period of time, bony fusion with the plug and opposed vertebrae. More recently, emphasis has been placed on fusing bone structures (i.e., adjoining vertebrae) with metallic or ceramic prosthetic cage implants. One fusion cage implant is disclosed in commonly assigned U.S. Pat. No. 5,026,373 to Ray et al., the contents of which are incorporated herein by reference. The Ray '373 fusion cage includes a cylindrical cage body having a thread formed as part of its external surface and apertures extending through its wall which communicate with an internal cavity of the cage body. The fusion cage is inserted within a tapped bore or channel formed in the intervertebral space thereby stabilizing the vertebrae and maintaining a predefined intervertebral space. Preferably, a pair of fusion cages are implanted within the intervertebral space. The adjacent vertebral bone structures communicate through the apertures and with bone growth inducing substances which are within the internal cavity to unite and eventually form a solid fusion of the adjacent vertebrae. FIGS. 1–2 illustrate the insertion of a pair of the Ray '373 fusion cages positioned within an intervertebral space.

SUMMARY OF THE INVENTION

Accordingly, the present invention is directed to further improvements in spinal fusion procedures. In accordance with a preferred embodiment, an apparatus for facilitating fusion of adjacent bony structures includes an implant body dimensioned for positioning between adjacent bone structures to maintain the bone structures in desired spaced relation during interbody fusion. The implant body has an outer wall and an external threaded configuration disposed on the outer wall. At least one concave surface at least partially extends along the implant body. The concave surface advantageously reduces the transverse cross-sectional dimension of the implant member thereby facilitating placement of the implant member in restricted intervertebral areas. In addition, the concave surface enables placement of a pair of implants in nested side-by-side relation. Preferably, the threaded configuration has portions removed along an arc section of the outer wall thereby defining a series of generally longitudinally aligned concave surfaces in individual turns thereof. A system and method for facilitating fusion of adjacent vertebrae is also disclosed.

BRIEF DESCRIPTION OF THE DRAWINGS

Preferred embodiment(s) of the present disclosure are described herein with reference to the drawings wherein:

FIG. 3 is a perspective view of the fusion implant apparatus in accordance with the principles of the present disclosure;

FIG. 4 is a side plan view of the implant apparatus;

FIG. 5 is an axial view of the implant apparatus;

FIG. 6 is a side cross-sectional view of the implant apparatus taken along the lines 6—6 of FIG. 5;

FIG. 7 is an axial cross-sectional view of the implant apparatus taken along the lines 7—7 of FIG. 4;

FIG. 8 is a view illustrating details of the threaded configuration of the implant apparatus;

DETAILED DESCRIPTION OF PREFERRED EMBODIMENTS

Figure 2:
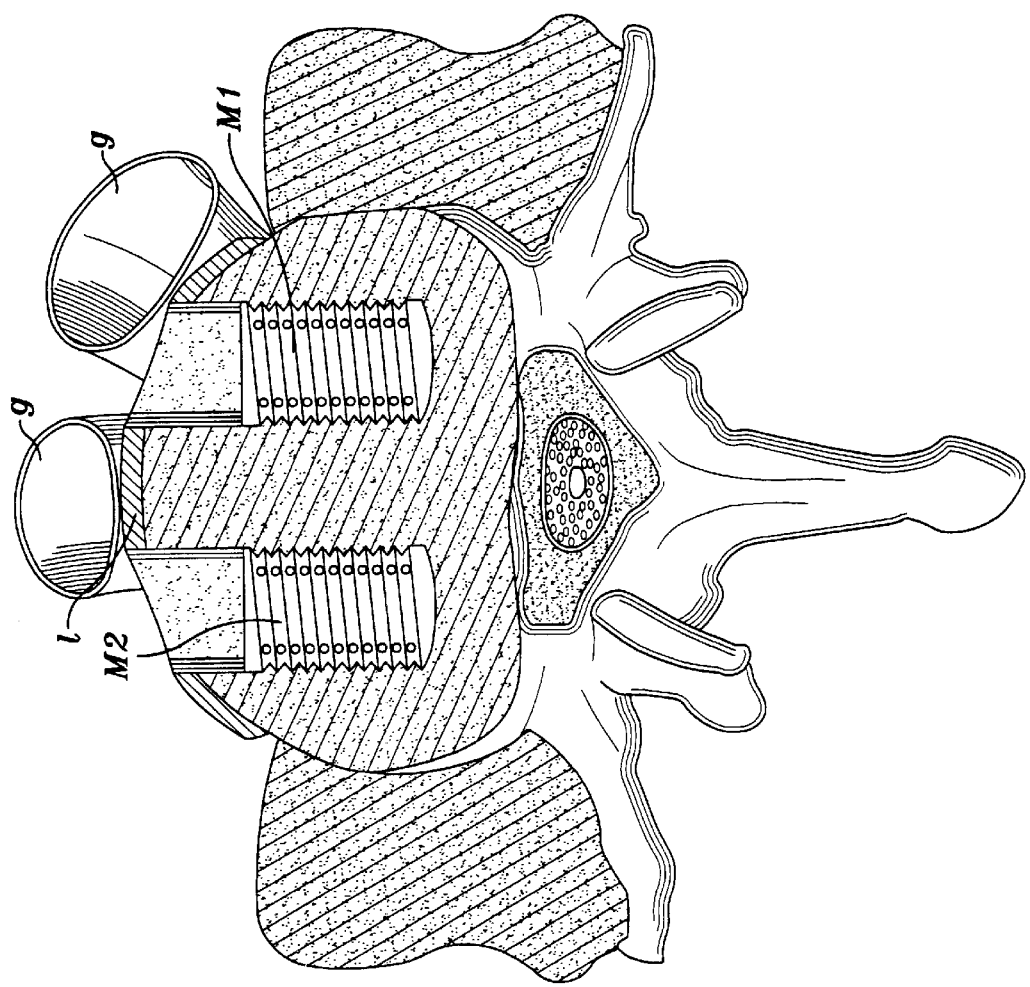
FIG. 2 is a view taken along line 2—2 of FIG. 1 illustrating a pair of prior art fusion implants positioned within the intervertebral space for fusion of adjacent vertebrae.
Figure 1:
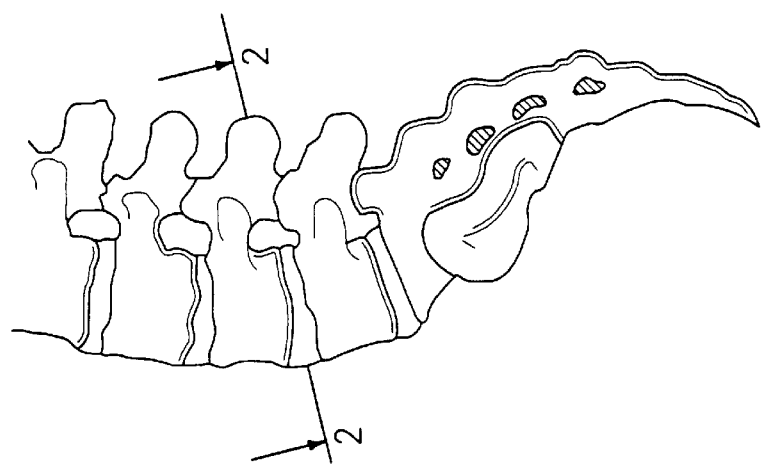
FIG. 1 is a view illustrating a portion of the vertebral column of a patient.

The preferred embodiment of the apparatus and method disclosed herein are discussed in terms of orthopedic spinal fusion procedures and instrumentation. It is envisioned, however, that the disclosure is applicable to a wide variety of procedures including, but, not limited to ligament repair, joint repair or replacement, non-union fractures, facial reconstruction and spinal stabilization. In addition, it is believed that the present method and instrumentation finds application in both open and minimally invasive procedures including endoscopic and arthroscopic procedures wherein access to the surgical site is achieved through a cannula or small incision.

The following discussion includes a description of the fusion implant utilized in performing a spinal fusion followed by a description of the preferred method for spinal fusion in accordance with the present disclosure.

In the discussion which follows, the term "proximal", as is traditional, will refer to the portion of the structure which is closer to the operator while the term "distal" will refer to the portion which is further from the operator.

Referring now to the drawings in which like reference numerals identify similar or identical elements throughout the several views, FIG. 3 illustrates, in perspective, the fusion implant apparatus of the present disclosure. Fusion implant 100 is intended to be inserted within a preformed bore in adjacent bone structures, e.g., adjacent vertebrae, with the bore spanning the intervertebral space and penetrating the vertebral end plates.

Fusion implant 100 includes elongated implant body 102 which is preferably fabricated from a suitable biocompatible rigid material such as titanium and/or alloys of titanium, stainless steel, ceramic materials or rigid polymeric materials. Implant body 102 is preferably sufficient in strength to at least partially replace the supporting function of an intervertebral disc, i.e., to maintain adjacent vertebrae in desired spaced relation, during healing and fusion.

With reference to FIGS. 3–7, implant body 102 includes exterior or outer wall 104 concentrically arranged about longitudinal axis "a" of the implant body 102 and inner cavity 106 within the exterior wall 104. Implant body 102 is preferably substantially cylindrical in configuration defining a constant diameter along its length. Inner cavity 106 is intended to accommodate bone growth inducing substances such as bone chips taken from allograft or autograft, etc . . . which facilitate the fusion process. Implant body 102 is preferably provided in various lengths ranging from about 18 mm–24 mm and in corresponding various diameters ranging from about 14 mm–18 mm. Other dimensions are also contemplated and may vary depending on the intended use of the implant in the cervical, thoracic or lumbar regions of the spine.

Outer wall 104 has an external threaded configuration 108 formed thereon. External threaded configuration 108 includes a uniform helical thread 110 which assists in advancing implant body 102 into a preformed channel provided in the adjacent vertebrae. In the preferred embodiment, thread 110 cooperates with an internally threaded bore within the adjacent vertebrae to advance implant. body 102 within the threaded bore. Alternatively, thread 110 may be a self-tapping cutting thread, i.e., the thread is capable of deburring bone material during advancement into the performed channel thereby precluding the requirement of tapping the internal bore in the vertebrae.

A plurality of apertures 112 extend through outer wall 104 of implant body 102. Apertures 112 are preferably formed by broaching grooves in the internal surface of the internal cavity 108. The effect of such broaching is to remove material from the valleys between the individual turn of the thread 110, thus defining the apertures 112. The advantages of such an arrangement are disclosed in U.S. Pat. No. 4,961,740, the contents of which are incorporated herein by reference, and include immediate bone to bone contact between the vertebral bodies or bone structures and the bone inducing substances packed within the internal cavity 108 of the implant body 102. Apertures 112 are preferably substantially the same in dimension although it is envisioned that the dimensions of the apertures may vary to provide for more or less bone to bone contact as desired.

As best depicted in FIGS. 4 and 7, apertures 112 are clustered about a transverse axis "t1", both at the upper and lower end of the axis. Consequently, apertures 112 come into contact with the upper and lower vertebral bone structures to encourage bone growth through implant body 102 from the vertebral bone structures when appropriately positioned within the vertebrae. The lateral sections of implant body 102 formed along transverse axis "t2" do not have apertures in order to prevent growth of disk material which might interfere with the bone. fusion process.

Outer wall 104 has a plurality of independent arcuate surfaces 114 defined in the outer wall and extending along the length of implant body 102. The arcuate surfaces 114 are preferably concave in configuration and may be formed by grinding, blasting applications, etc. Preferably, concave surfaces 114 extend radially inwardly within each thread turn without penetrating or extending into the outer wall surface thereby defining removed portions of the thread as shown.

The concave surface arrangement provides two specific advantages. First, such arrangement increases the pull out or expulsion force necessary to remove the implant from the adjacent vertebrae. Secondly, the. concave surface arrangement permits a pair of implants to be positioned in side by side relation within the adjacent vertebrae in a nested contacting relation. Moreover, the concave surface arrangement provides a reduced cross-sectional dimension along second transverse axis "t2" relative to the cross-sectional dimension along first transverse axis "t1" thereby facilitating placement of the implant body 102 within restricted vertebral locations.

Implant body 102 defines entry and trailing end faces 116, 118. End faces 116, 118 are preferably open, i.e, having apertures 120, 122 therein in communication with the inner cavity 106. As best depicted in FIG. 6, implant body 102 has internal annular recesses 124 adjacent each end face 116, 118. Annular recesses 124 are intended to receive plastic end caps 126 (FIG. 3) which are received within the recesses in snap-fit relation therewith to enclose internal cavity 108 thereby retaining the bone.growth inducing substances therein. Implant body 102 further includes tool receiving structure in the form of longitudinal extending internal rails 128 extending the length of the implant body 102 in diametrically opposed relation. Rails 128 receive correspondingly dimensioned prongs of an insertion instrument such that the insertion instrument may be rotated to cause corresponding rotation and entry of implant body 102 into the intervertebral space.

Alternate Embodiment(s)

Figure 10:
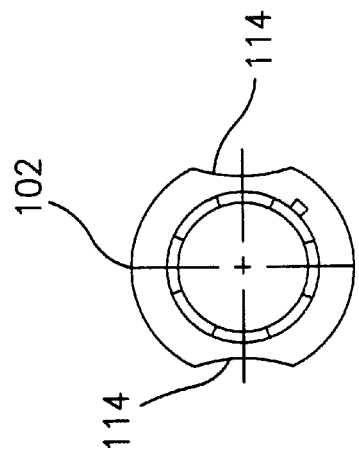
FIG. 10 is an axial view of the implant apparatus of FIG. 9.
Figure 9:
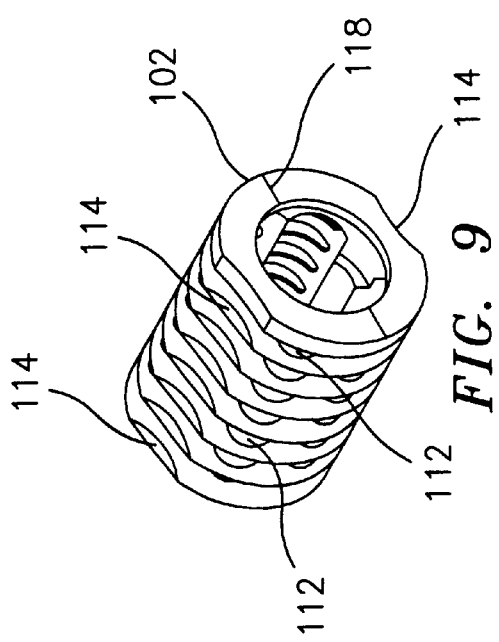
FIG. 9 is a perspective view of an alternate embodiment of the implant apparatus of FIG. 3.

FIGS. 9–10 illustrate an alternate embodiment of the implant apparatus of FIG. 3. This implant apparatus is substantially similar to the apparatus disclosed in FIG. 3, but, however incorporates a second series of concave surfaces 114 disposed in diametrically opposed relation to the first series. The second series provides flexibility to the user in terms of placement of the implant within the desired orientation within the intervertebral disc space. The second series also significantly reduces the cross-sectional dimension of the implant body along the second transverse axis "t2".

Figure 11:
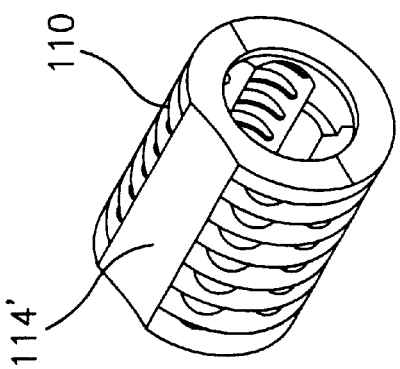
FIG. 11 is a perspective view of another alternate embodiment of the implant apparatus of FIG. 3.

FIG. 11 illustrates an alternate embodiment of the implant apparatus of FIG. 3 where the concave surface extends through threaded configuration 110 and into exterior wall 104 thereby defining a single concave surface 114' which extends along the length of implant body 102.

Insertion of Fusion Implant

The insertion of the fusion implant 100 into an intervertebral space defined between adjacent lumbar vertebrae will now be described. The subsequent description will be particularly discussed in conjunction with an open posterior approach for spinal fusion implant insertion. However, it is to be appreciated that other approaches, e.g., anterior, lateral, posterior lateral, anterior lateral etc . . . could be utilized. Laparoscopic approaches are also envisioned.

Figure 12:
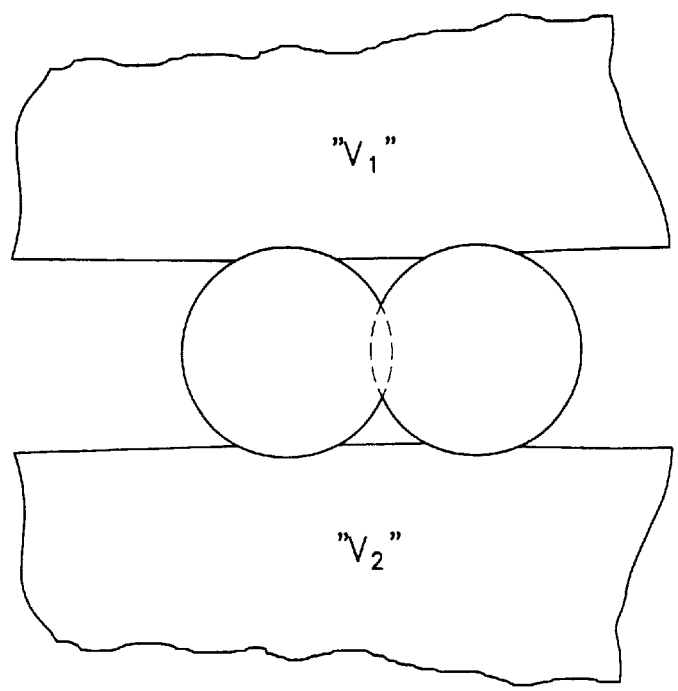
FIGS. 12–14 are views illustrating a preferred sequence of the implant apparatus within adjacent vertebrae.

Initially, a first lateral side of the intervertebral space "i" is accessed utilizing appropriate retractors to expose the posterior vertebral surface. A drilling instrument is selected to prepare the disc space and vertebral end plates for insertion of the fusion implant. The cutting depth of drilling instrument may be adjusted as desired. The drilling instrument is advanced into the intervertebral space adjacent to the first lateral side to shear the soft tissue and cut the bone of the adjacent vertebrae thereby forming a bore which extends into the adjacent vertebrae adjacent the first lateral side as depicted in FIG. 12. With the first bore "b1" drilled in the first lateral side, attention is directed to forming the bore in the second lateral side. With continued reference to FIG. 12, the second lateral side is accessed and the center entry point for the drill is identified. Preferably, the drill is positioned such that the second bore "b2" will overlap the first bore "b1". The drill is activated to form the second bore. The first and second bores "b1, b2" may be tapped with a conventional tap instrument if desired.

Figure 13:
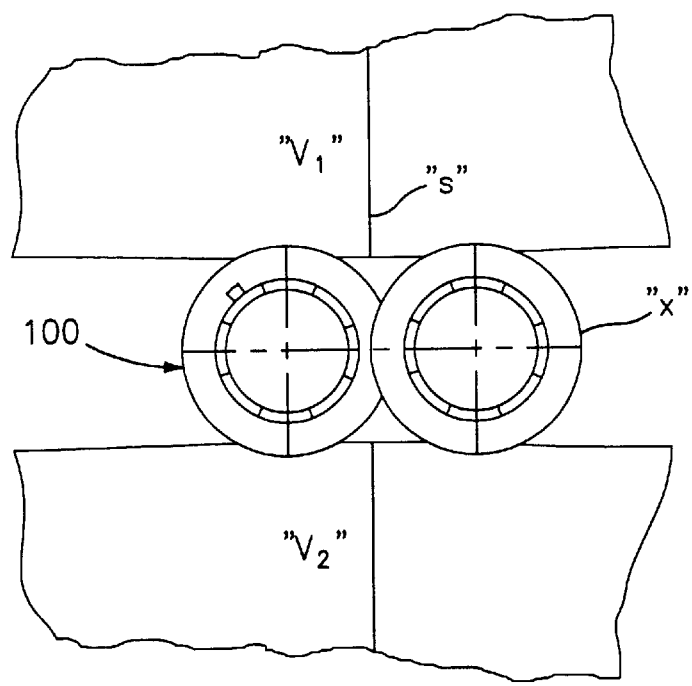

With reference to FIG. 13, a first implant 100 is packed with bone growth inducing substances as is conventional in the art. The fusion implant 100 may then be mounted on an insertion instrument (not shown) and advanced within the intervertebral space by rotating the implant 100 whereby threaded configuration 110 of the implant body 102 cooperates with the threaded bore to advance within the intervertebral space "i". Preferably, the implant 100 is arranged such that concave surface generally extends along the axis "s" of the spine and faces the midline of the intervertebral space. If the implant of FIGS. 9–10 is utilized, the second series of concave surfaces facilitates placement of the implant 100 with the concave surface arrangement adjacent to the midline of the intervertebral space, i.e., when positioned, the implant need only be rotated a maximum of 90° in either direction to place the concave surface arrangement adjacent the midline. With the first implant positioned within the intervertebral space, a second implant "x" is implanted within the second threaded bore in the same manner. The second implant "x" is preferably a conventional cylindrical implant such as the implant disclosed in the Ray '373 patent. As appreciated, although the second bore overlaps the first bore, the clearance provided by the concave surface arrangement of the first implant 100 permits the second implant "x" to be advanced within the intervertebral space without interference. The second implant "x" is arranged such that the outer convex surface is received within the concave surface area of the first implant in nested side-by-side relation as shown. Thus, the concave surface arrangement permits two implants 100, "x" to be placed in nested side-by-side arrangement. The concave surface arrangement also reduces the effective cross-sectional dimension of implant 100 thereby facilitating placement of the implants in a restricted vertebral location.

Figure 14:
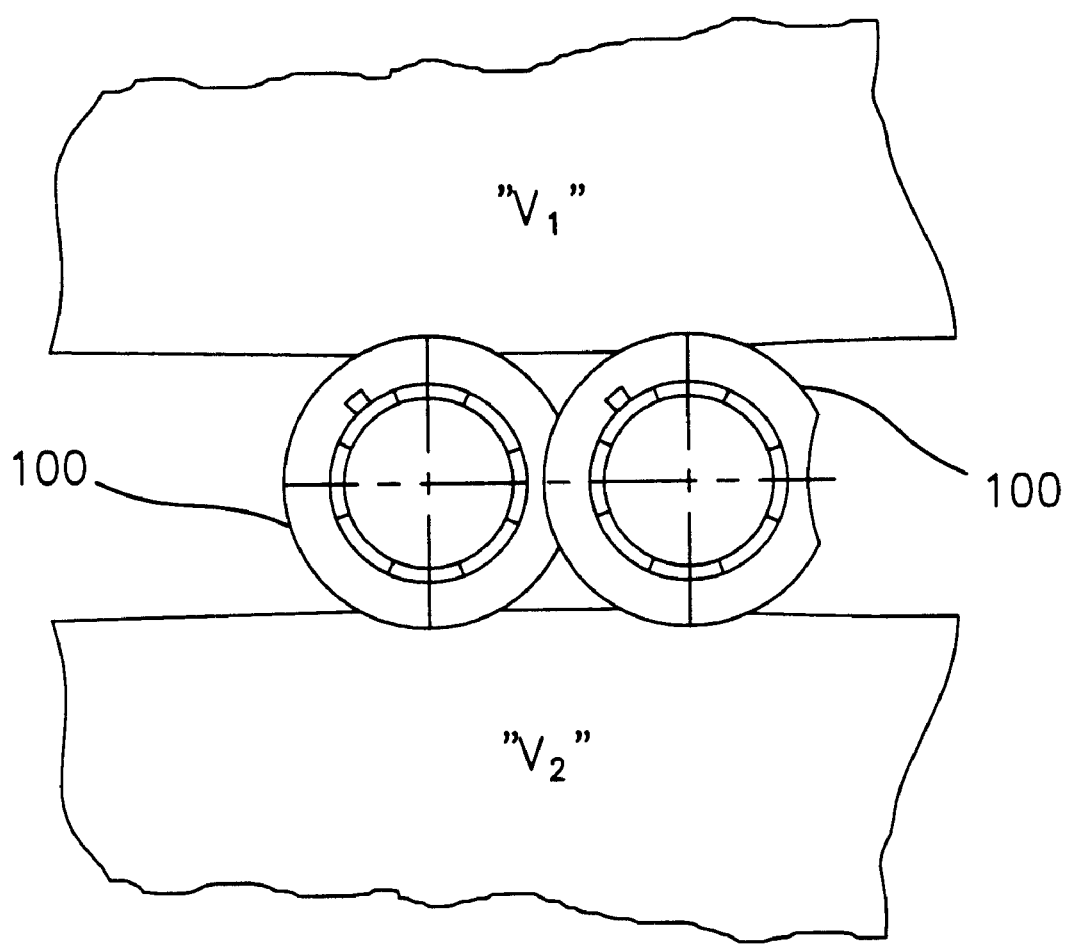

With reference to FIG. 14, it is appreciated that the second implant may be identical to implant 100. When positioned within the adjacent vertebrae, the concave surface area may be facing the midline of the intervertebral space or alternatively adjacent the outer portion of the space as shown in phantom.

Implants 100 form struts across the intervertebral space "i" to maintain the adjacent vertebrae "$V_1, V_2$" in appropriate spaced relation during the fusion process. Over a period of time, the adjacent vertebral tissue communicates through apertures 112 within implants 100 to form a solid fusion. Desirably, lateral vertebral tissue growth into the implant 100 is restricted due to the concave surface areas of the implant being devoid of apertures. Such lateral growth would inhibit the fusion process and potentially restrict subsequent spinal mobility.

While the above description contains many specifics, these specifics should not be construed as limitations on the scope of the disclosure, but merely as exemplifications of preferred embodiments thereof. For example, the fusion implant 100 could also be used for thoracic and cervical vertebrae. Those skilled in the art will envision many other possible variations that are within the scope and spirit of the disclosure as defined by the claims appended hereto.

What is claimed is:

1. An apparatus for facilitating fusion of adjacent vertebrae, which comprises an implant body dimensioned for positioning within an intervertebral space defined between adjacent vertebrae, the implant body including an outer wall defining a longitudinal axis and at least one thread disposed on the outer wall for facilitating insertion of the implant body within the intervertebral space, the at least one thread having a concave recess defined therein extending radially inwardly relative to the longitudinal axis of the implant body to a depth which is less than a corresponding height of the at least one thread.

2. The apparatus according to claim 1 wherein the at least one thread includes a plurality of individual concave recesses disposed in general longitudinal alignment.

3. The apparatus according to claim 2 wherein the implant body defines substantially circular cross-section.

4. The apparatus according to claim 2 wherein the implant body is substantially cylindrical.

5. The apparatus according to claim 4 wherein the outer wall of the implant body defines an internal cavity for accommodating bone growth inducing substances and having a plurality of apertures extending through the outer wall in communication with the internal cavity.

6. An apparatus for supporting adjacent vertebrae, which comprises:

a first implant body dimensioned for positioning within an intervertebral space defined between adjacent vertebrae to maintain the adjacent vertebrae in predetermined spaced relation during healing, the first implant body including an outer wall defining a longitudinal axis and a threaded configuration, the threaded configuration dimensioned to engage bone tissue of the adjacent vertebrae upon rotation of the first implant body to facilitate advancement within the intervertebral space, the first implant body including a plurality of interrupted concave recesses disposed in spaced relation along the longitudinal axis and arranged in general longitudinal alignment with respect to the longitudinal axis, the concave recesses extending radially inwardly to a depth less than a height of a thread of the threaded configuration, the first implant body being dimensioned to reduce an overall cross sectional dimension of the first implant body to thereby facilitate positioning within the intervertebral space.

7. The apparatus according to claim 6 including first and second series of the interrupted concave recesses disposed in diametrical opposed relation.

8. The apparatus according to claim 6 wherein the outer wall of the first implant body defines an internal cavity for accommodating bone growth inducing substances and having a plurality of apertures extending through the outer wall in communication with the internal cavity.

9. The apparatus according to claim 8 including a second implant body defining a longitudinal axis and having an arcuate outer wall portion correspondingly dimensioned to be received within the concave recesses of the first implant body to permit the first and second implant bodies to be positioned in nested side by side relation within the intervertebral space defined between the adjacent vertebrae.

* * * * *